(12) United States Patent
Steinbrenner et al.

(10) Patent No.: US 6,984,766 B2
(45) Date of Patent: Jan. 10, 2006

(54) METHOD FOR SIDE-CHAIN ALKYLATION OR ALKENYLATION

(75) Inventors: Ulrich Steinbrenner, Neustadt (DE); Ralf Böhling, Griesheim (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 449 days.

(21) Appl. No.: 10/344,519

(22) PCT Filed: Aug. 10, 2001

(86) PCT No.: PCT/EP01/09296

§ 371 (c)(1),
(2), (4) Date: Feb. 12, 2003

(87) PCT Pub. No.: WO02/14241

PCT Pub. Date: Feb. 21, 2002

(65) Prior Publication Data

US 2004/0106834 A1    Jun. 3, 2004

(30) Foreign Application Priority Data

Aug. 17, 2000   (DE) .................................. 100 40 184

(51) Int. Cl.
*C07C 2/68*    (2006.01)

(52) U.S. Cl. ........................................ 585/950; 585/452
(58) Field of Classification Search ................ 585/950, 585/452

See application file for complete search history.

(56) References Cited

U.S. PATENT DOCUMENTS

| | | |
|---|---|---|
| 2,448,641 A | 9/1948 | Whitman |
| 3,291,847 A | 12/1966 | Phillips |
| 4,914,250 A | 4/1990 | Smith |
| 5,104,843 A | 4/1992 | Staton et al. |
| 5,329,058 A | 7/1994 | Shimada et al. |

FOREIGN PATENT DOCUMENTS

GB    1 269 280    4/1972

*Primary Examiner*—Thuan D Dang
(74) *Attorney, Agent, or Firm*—Novak Druce & Quigg; Jason D. Voight

(57) ABSTRACT

In a process for reducing the formation of polymers during side-chain alkylation or side-chain alkenylation of alkylaromatic compounds by reaction with olefins or diolefins in the presence of an alkali metal catalyst followed by distillation in order to isolate the alkylated or alkenylated compound, the alkali metal is present in the catalyst on an inorganic support, and the catalyst is mechanically separated from the reaction mixture after the reaction and before the distillation.

10 Claims, No Drawings

METHOD FOR SIDE-CHAIN ALKYLATION OR ALKENYLATION

The present invention relates to a process for reducing the formation of polymers during side-chain alkylation or side-chain alkenylation of alkylaromatic compounds.

Side-chain alkylation, in particular of aromatic compounds carrying an acidic proton in the α-position of the side chain, in the presence of catalysts is known.

U.S. Pat. No. 2,448,641 describes a process, in particular, for the side-chain alkylation of toluene. The catalyst employed here is from 0.1 to 20% of an alkali metal, based on toluene. It is described that the catalyst can be separated off from the reaction product by filtration, after which the product is purified by fractional distillation. The preferred catalyst employed is sodium.

U.S. Pat. No. 3,291,847 describes, in particular, the potassium-catalyzed alkylation of toluene using propene. The catalyst employed is potassium, sodium or a sodium/potassium alloy together with graphite on sodium carbonate as support. The catalyst is, in particular, formed in situ in the reactor. It is described that, due to the combination of the alkali metal with graphite and the support, a brown tar-like polymer is not formed in the reactor, which is the case without use of a catalyst support. It is described that the catalyst can be removed from the reaction mixture after the reaction by filtration. The catalyst can also or thereafter be deactivated by reaction with a polar compound, such as an alcohol. Unreacted starting materials can be recovered and recycled into the reaction. According to the examples, the catalyst is deactivated in the reaction mixture by quenching with an alcohol.

U.S. Pat. No. 4,914,250 relates to a process, in particular, for the alkenylation of toluene using propene in the presence of a supported potassium or potassium alloy catalyst using sodium hydroxide or potassium hydroxide as cocatalyst. The suitable support materials mentioned are diatomaceous earth, activated carbon, carbon, silicon dioxide, aluminum oxide, etc. The catalyst is deactivated after the reaction by reaction with methanol.

It has been found that on deactivation of the catalyst in the reaction mixture by protolysis, subsequent distillation of the product mixture results in formation of tar-like polymers in the distillation still. This makes separation and purification of the reaction product much more difficult.

Removal of the catalyst from the reaction mixture is particularly difficult to carry out in the case of unsupported catalysts, which means that catalyst residues may enter the distillation.

It is an object of the present invention to provide a process for reducing the formation of polymers during side-chain alkylation or side-chain alkenylation of alkylaromatic compounds.

We have found that this object is achieved by a process for reducing the formation of polymers during side-chain alkylation or side-chain alkenylation of alkyl-aromatic compounds by reaction with olefins or diolefins in the presence of an alkali metal catalyst followed by distillation in order to isolate the alkylated or alkenylated compound, where the alkali metal is present in the catalyst on an inorganic support, and the catalyst is mechanically separated from the reaction mixture after the reaction and before the distillation. Thus, only the organic phase mechanically separated off from the catalyst is fed to the distillation, without the catalyst having been protolyzed.

It has been found in accordance with the invention that work-up of the reaction mixture by distillation is significantly simplified if the catalyst is mechanically separated off from the product mixture without protolysis. In this case, no tar-like polymers, which would cause major technical problems, arise in the still of a subsequent distillation column.

In particular, (spent) mechanically separated catalyst can be protolyzed, with an organic phase formed in the protolysis not being fed back into the distillation.

In addition, it has been found that the use of alkali metal carbonates, alkali metal halides or mixtures thereof as catalyst support allows complete removal of the alkali metal catalyst from the reaction mixture by simple filtration.

The mechanical removal of the catalyst is preferably carried out using a mixer/settler, settler, filter or cross-flow filter, depending on the particular design of the reaction apparatus.

The alkali metal catalyst can thus be removed completely from the reaction mixture before distillation of the reaction mixture. This substantially, preferably completely, prevents the formation of tar-like polymers in the distillation apparatus.

The catalyst support is particularly preferably selected from K2CO3, K2CO3/KCl and K2CO3/NaCl. The alkali metal applied to the support is preferably sodium, potassium or an NaK alloy. Sodium is preferably employed on the support.

The preparation of the supported catalyst is known and can be carried out as described, for example, in DE-A-197 15 203. The catalyst here preferably contains from 0.5 to 20% by weight, in particular from 1 to 15% by weight, of metallic sodium and/or potassium, based on the entire catalyst.

In the process as a whole, the catalyst is prepared, before use in the reaction, from alkali metal and support at temperatures above 100° C. It may additionally be activated using hydrogen and/or alkylaromatic compounds at temperatures above 100° C.

The reaction can be carried out batchwise or preferably continuously. Suitable apparatuses are stirred-tank reactors, stirred-tank reactor cascades, stirred columns, loop reactors, cascades of loop reactors or similar apparatuses. The catalyst can be employed as a suspension or fluidized bed, preferably as a suspension. The catalyst here is preferably retained, as described above, by a mixer/settler, a settler, a filter, a cross-flow filter or a similar technical unit. Particular preference is given to filter devices. The residence time of the catalyst in the reaction step is significantly longer than the organic phase, i.e. the catalyst is retained and used further until a loss in activity.

When the reaction and removal of the catalyst are complete, the product mixture is separated by distillation. Unreacted starting materials can be fed back into the reaction. The alkylated or alkenylated product can then be further purified by further methods, for example by fractional distillation, fractional crystallization, extraction, etc.

The reaction is preferably carried out continuously by the suspension method, with the catalyst being retained in the reactor. The reaction is preferably carried out with vigorous stirring.

The reaction is generally carried out at a temperature of from −50 to 400° C., preferably at a temperature of from −20 to 300° C., particularly preferably from 80 to 250° C., in particular from 100 to 200° C., and at a pressure of preferably from 0.1 to 200 bar, particularly preferably from 1 to 150 bar, in particular from 1 to 100 bar, preferably in the liquid phase without a gas phase.

The alkylaromatic compounds employed here are all suitable alkylaromatic compounds. They may contain as aromatic nucleus a benzene or naphthalene nucleus, for example. Furthermore, alkylalicyclic compounds, in which the cyclic nucleus may be a cyclic alkyl, alkenyl or alkynyl radical, are furthermore suitable. Radicals in which a number of the ring structures are linked to one another may also be employed. The ring structures have an acidic hydrogen atom in the α-position of the side chain. They preferably contain at least one alkyl radical bonded to the cyclic structure. The alkyl radicals here may have any desired length and be substituted by further substituents. The alkylaromatic compounds are preferably benzenes substituted by from 1 to 6, preferably from 1 to 3, in particular from 1 to 2, C1–20-alkyl, preferably C1–3-alkyl radicals, naphthalenes substituted by from 1 to 10, preferably from 1 to 5, particularly preferably from 1 to 2, C1–20-alkyl, preferably C1–3-alkyl radicals, and the alkylalicyclic compounds employed are cyclopentenes or cyclohexenes substituted by from 1 to 5, preferably 1 or 2, or from 1 to 6, preferably from 1 to 3, in particular 1 or 2, C1–20-alkyl, preferably C1–3-alkyl radicals respectively.

The olefins preferably have from 2 to 20, particularly preferably from 2 to 10, in particular from 2 to 5, carbon atoms. Preference is given to ethene, propene, 1-butene, 2-butene, isobutene, 1-pentene, 2-pentene, 2-methyl-1-butene, 2-methyl-2-butene and/or 3-methyl-1-butene. Particular preference is given to ethene and propene. The diolefins preferably have from 4 to 20, particularly preferably from 4 to 10, in particular from 4 to 6, carbon atoms. Particular preference is given to butadiene and/or isoprene.

Particular preference is given to the reaction of toluene with ethene or propene to give propylbenzene or isobutylbenzene, the reaction of cumene with ethene to give tert-amylbenzene and the reaction of xylenes with butadiene to give 5-tolylpentenes.

Spent catalyst can be discharged from the reactor, protolyzed and then disposed of. The addition of salt to the alkali metal in combination with a filter prevents alkali metal escaping from the reactor into the work-up step, where it would result in major technical and safety-relevant problems.

The invention also relates to the use of alkali metal catalysts supported on an inorganic support in the side-chain alkylation or side-chain alkenylation of alkylaromatic compounds by reaction with olefins or diolefins followed by distillation in order to reduce the formation of polymers during the distillation.

The invention is explained in greater detail below with reference to examples.

EXAMPLES

Preparation of the Catalyst 35 g of KCl and 35 g of K2CO3 were combined and dried overnight at 300° C. in a stream of argon. 10.8 g of Na were then added, and the metal was supported onto the potassium salts at 300° C. for 2 hours. The finished catalyst was subsequently dispersed in 115 g of toluene and transferred into a stirred-tank reactor with an internal capacity of 270 ml.

Experimental Procedure 0.117 mol/h of dry liquid propene and 0.316 mol/h of dry toluene were pumped continuously into a reactor for 160 hours at 130° C. and then for 80 hours at 160° C., and the reaction product was drawn off via a 4 μm filter. A magnetically coupled stirrer with impeller turbine and a speed of from 1000 to 1200 rpm kept the catalyst in suspension. After decompression to ambient pressure, 7.6 kg of product having the composition listed in Table 1 were obtained. Na and K were neither visible nor detectable (<10 ppm by weight) in the product stream.

75 ml of the resultant reaction product (composition see table) were heated at 250° C. for 72 hours in a glass pressure autoclave. The organic phase turned a pale yellow color, and no visible deposits occurred.

75 ml of the reaction product were mixed with 15 ml of 30% aqueous NaOH, and heated at 250° C. for 72 hours in a glass pressure autoclave with stirring. The organic phase turned a pale yellow color, and likewise no visible deposits occurred.

For comparison with the known procedure, the contents of the steel autoclave were mixed with EtOH/H2O under argon, and the organic phase (88 g, composition see Table 1) was heated at 250° C. for 72 hours in a glass pressure autoclave with stirring. The solution turned a dark brown color, and black, tacky, tar-like deposits formed.

TABLE 1

Composition of the organic phase according to GC analysis

| | Product [% by wt.] | Org. phase after protolysis of the catalyst [% by wt.] |
|---|---|---|
| Propene | 1.262 | 0.032 |
| Ethanol | 0.000 | 0.56 |
| Hexene isomers | 0.890 | 0.136 |
| Toluene | 74.3 | 53.2 |
| Isobutylbenzene | 21.6 | 18.6 |
| n-Butylbenzene | 1.72 | 0.993 |
| 1- and 2-Methylindane | 0.898 | 1.05 |
| Methylindenes | 0.000 | 4.51 |
| High-boiling components | Remainder | remainder |

Comparative Experiment (Without Addition of Salt)

5.86 kg of NaK2 and 45 g of toluene were introduced into a stirred-tank reactor with an internal capacity of 100 ml. The autoclave was subsequently flooded with toluene, and 0.044 mol/h of dry liquid propene and 0.119 mol/h of dry toluene were pumped continuously at 130° C., and the reaction product was discharged via a 2 μm filter. A magnetically coupled stirrer with impeller turbine and a speed of 1200 rpm kept the catalyst in suspension. The experiment had to be terminated after a few hours since significant amounts (a few hundred milligrams) of liquid NaK2 had escaped from the reactor.

We claim:

1. A process for reducing the formation of polymers during side-chain alkylation or side-chain alkenylation of alkylaromatic compounds by reaction with olefins or diolefins in the presence of an alkali metal catalyst wherein the alkali metal is present in the catalyst on an inorganic support, and the catalyst is mechanically separated from the reaction mixture after the reaction, followed by protolyzation of the reaction mixture thus obtained, followed by distillation in order to isolate the alkylated or alkenylated compound.

2. A process as claimed in claim 1, wherein the mechanical separation of the catalyst is carried out using a mixer/settler, settler, filter or cross-flow filter.

3. A process as claimed in claim 1, wherein the inorganic support employed is an alkali metal carbonate, alkali metal halide or a mixture thereof.

4. A process as claimed in claim 3, wherein the support is selected from K2CO3, K2CO3/KCl and K2CO3/NaCl.

5. A process as claimed in claim 1, wherein the reaction is carried out continuously by the suspension method, and the catalyst is retained in the reactor.

6. A process as claimed in claim 1, wherein toluene is reacted with propene.

7. A process as claimed in claim 1, wherein the reaction is carried out in the liquid phase at a temperature in the range from 100 to 200° C.

8. A process as claimed in claim 1, wherein spent mechanically separated catalyst is protolyzed and an organic phase formed in the protolysis is not fed back into the distillation.

9. A process as claimed in claim 1, wherein the protolyzation of the reaction mixture is performed by adding aqueous NaOH.

10. A process as claimed in claim 9, wherein the aqueous NaOH is 30%.

* * * * *